(12) United States Patent
Fleming

(10) Patent No.: US 10,772,750 B2
(45) Date of Patent: Sep. 15, 2020

(54) CANNULATION GUIDING DEVICE FOR BIFURCATED STENT AND METHOD OF USE

(71) Applicant: CARDINAL HEALTH SWITZERLAND 515 GMBH, Bar Zug (CH)

(72) Inventor: James A Fleming, Bethlehem, PA (US)

(73) Assignee: CARDINAL HEALTH SWITZERLAND 515 GMBH, Bar Zug (SE)

( * ) Notice: Subject to any disclaimer, the term of this patent is extended or adjusted under 35 U.S.C. 154(b) by 226 days.

(21) Appl. No.: 16/049,196

(22) Filed: Jul. 30, 2018

(65) Prior Publication Data

US 2018/0333283 A1 Nov. 22, 2018

Related U.S. Application Data

(63) Continuation of application No. 13/836,189, filed on Mar. 15, 2013, now Pat. No. 10,039,657.
(Continued)

(51) Int. Cl.
*A61F 2/954* (2013.01)
*A61F 2/966* (2013.01)
(Continued)

(52) U.S. Cl.
CPC .............. *A61F 2/954* (2013.01); *A61F 2/856* (2013.01); *A61F 2/966* (2013.01); *A61F 2/07* (2013.01); *A61F 2002/065* (2013.01); *A61F 2002/067* (2013.01); *A61F 2002/9511* (2013.01); *A61F 2220/0075* (2013.01)

(58) Field of Classification Search
CPC .......... A61F 2/954; A61F 2/856; A61F 2/966; A61F 2002/067; A61F 2/07
See application file for complete search history.

(56) References Cited

U.S. PATENT DOCUMENTS 5,556,414 A 9/1996 Turi
5,957,929 A 9/1999 Brenneman
(Continued)

FOREIGN PATENT DOCUMENTS

CN 1561240 A 1/2005
CN 1870951 A 11/2006
(Continued)

OTHER PUBLICATIONS

European Search Report for Application No. EP13198750, dated May 22, 2014, 6 pages.
(Continued)

*Primary Examiner* — Julian W Woo
(74) *Attorney, Agent, or Firm* — Arent Fox LLP

(57) ABSTRACT

The present invention is directed to an intraluminal guiding device having an expandable guiding member so as to facilitate and overcome the difficulties associated with obtaining contra-lateral leg access of a bifurcated stent or a bifurcated stent graft with a second guidewire and a method for treating abdominal aortic aneurysms with such a device. The guiding device comprises a pre-loaded second wire positioned within the contra-lateral leg which facilitates access to said leg in accordance with the present invention.

11 Claims, 14 Drawing Sheets

Related U.S. Application Data

(60) Provisional application No. 61/740,538, filed on Dec. 21, 2012.

(51) Int. Cl.
*A61F 2/856* (2013.01)
*A61F 2/07* (2013.01)
*A61F 2/06* (2013.01)
*A61F 2/95* (2013.01)

(56) References Cited

U.S. PATENT DOCUMENTS

| | | | |
|---|---|---|---|
| 6,224,609 B1 | 5/2001 | Ressemann et al. | |
| 6,458,152 B1 | 10/2002 | Khosravi et al. | |
| 6,478,813 B1 | 11/2002 | Keith et al. | |
| 6,669,718 B2 | 12/2003 | Besselink | |
| 7,235,083 B1 | 6/2007 | Perez et al. | |
| 7,998,186 B2 * | 8/2011 | Hartley | A61F 2/07 623/1.11 |
| 8,118,862 B2 | 2/2012 | Saeed | |
| 8,475,513 B2 | 7/2013 | Sithian | |
| 8,821,567 B2 | 9/2014 | Saeed | |
| 2001/0049534 A1 | 12/2001 | Lachat | |
| 2004/0153119 A1 | 8/2004 | Kusleika et al. | |
| 2005/0021132 A1 | 1/2005 | Bolduc et al. | |
| 2005/0182476 A1 * | 8/2005 | Hartley | A61F 2/07 623/1.11 |
| 2007/0043425 A1 | 2/2007 | Hartley et al. | |
| 2007/0299498 A1 | 12/2007 | Perez et al. | |
| 2008/0221664 A1 | 9/2008 | Bales et al. | |
| 2009/0099649 A1 | 4/2009 | Chobotov et al. | |
| 2009/0299462 A1 | 12/2009 | Fawzi et al. | |

FOREIGN PATENT DOCUMENTS

| | | |
|---|---|---|
| CN | 101448540 A | 6/2009 |
| CN | 101917929 A | 12/2010 |
| WO | 9624308 A1 | 8/1996 |
| WO | 9703624 A1 | 2/1997 |
| WO | 9849983 A1 | 11/1998 |
| WO | 2004066874 A1 | 8/2004 |
| WO | 2010064244 A2 | 6/2010 |
| WO | 2011008538 A1 | 1/2011 |
| WO | 2012068257 A2 | 5/2012 |

OTHER PUBLICATIONS

Examination Report for Australian Application No. AU2013270547 filed Dec. 12, 2013.
Examination Report for Australian Application No. AU2013270556 filed Dec. 12, 2013.
Extended European Search Report for Application No. EP13198728.1 dated May 13, 2014, 10 pages.
Extended European Search Report for Application No. EP15175716.8 dated Sep. 29, 2015, 8 pages.
Extended European Search Report for Application No. EP18156562, dated Nov. 2, 2018, 8 pages.
Office Action for corresponding Chinese Patent Application No. 201310713650.6 dated Jun. 9, 2017, 14 pages.
Office Action in corresponding Chinese Patent Application No. 201310713650.6 dated Oct. 9, 2016, 12 pages.
Office Action dated Aug. 22, 2017 for Japanese Application No. JP2013263680 filed Dec. 20, 2013, 5 pages.
Office Action with English translation for corresponding Chinese Patent Application No. 201310713680.7 dated Jul. 24, 2017, 12 pages.
Office Action with English translation for corresponding Chinese Patent Application No. 201310713680.7 dated Oct. 9, 2016, 26 pages.
Summons to Attend Oral Proceedings Pursuant for European Application No. EP13198750.5, dated Dec. 2, 2016, 5 pages.

* cited by examiner

CANNULATION GUIDING DEVICE FOR BIFURCATED STENT AND METHOD OF USE

CROSS REFERENCE TO RELATED APPLICATION

This application is a continuation of U.S. Pat. No. 10,039,657 issued Aug. 7, 2018, which claims the benefit of U.S. Provisional Application, Ser. No. 61/740,538 filed Dec. 21, 2012, both of which are incorporated by reference herein.

BACKGROUND OF THE INVENTION

Field of the Invention

The present invention relates to abdominal aortic aneurismal devices and more particularly to a guiding device of the delivery system which facilitates cannulation of the contra-lateral leg of a Bifurcated Stent or Bifurcated Stent Graft in-vivo and the method of use.

Discussion of the Related Art

An aneurysm is an abnormal dilation of a layer or layers of an arterial wall, usually caused by a systemic collagen synthetic or structural defect. An abdominal aortic aneurysm is an aneurysm in the abdominal portion of the aorta, usually located in or near one or both of the two iliac arteries or near the renal arteries. The abdominal aortic aneurysm often arises in the infrarenal portion of the diseased aorta, for example, below the kidneys. A thoracic aortic aneurysm is an aneurysm in the thoracic portion of the aorta. When left untreated, the aneurysm may rupture, usually causing rapid fatal hemorrhaging.

Aneurysms may be classified or typed by their position as well as by the number of aneurysms in a cluster. Typically, abdominal aortic aneurysms may be classified into five types. A Type I aneurysm is a single dilation located between the renal arteries and the iliac arteries. Typically, in a Type I aneurysm, the aorta is healthy between the renal arteries and the aneurysm, and between the aneurysm and the iliac arteries.

A Type II A aneurysm is a single dilation located between the renal arteries and the iliac arteries. In a Type II A aneurysm, the aorta is healthy between the renal arteries and the aneurysm, but not healthy between the aneurysm and the iliac arteries. In other words, the dilation extends to the aortic bifurcation. A Type II B aneurysm comprises three dilations. One dilation is located between the renal arteries and the iliac arteries. Like a Type II A aneurysm, the aorta is healthy between the aneurysm and the renal arteries, but not healthy between the aneurysm and the iliac arteries. The other two dilations are located in the iliac arteries between the aortic bifurcation and the bifurcations between the external iliacs and the internal iliacs. The iliac arteries are healthy between the iliac bifurcation and the aneurysms. A Type II C aneurysm also comprises three dilations. However, in a Type II C aneurysm, the dilations in the iliac arteries extend to the iliac bifurcation.

A Type III aneurysm is a single dilation located between the renal arteries and the iliac arteries. In a Type III aneurysm, the aorta is not healthy between the renal arteries and the aneurysm. In other words, the dilation extends to the renal arteries.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft via transperitoneal or retroperitoneal procedure has been the standard treatment, it is associated with significant risk. For example, complications may include peri-operative myocardial ischemia, renal failure, erectile impotence, intestinal ischemia, infection, lower limb ischemia, spinal cord injury with paralysis, aorta-enteric fistula, and death. Surgical treatment of abdominal aortic aneurysms is associated with an overall mortality rate of five percent in asymptomatic patients, sixteen to nineteen percent in symptomatic patients, and is as high as fifty percent in patients with ruptured abdominal aortic aneurysms.

Disadvantages associated with conventional surgery, in addition to the high mortality rate, include an extended recovery period associated with the large surgical incision and the opening of the abdominal cavity, difficulties in suturing the graft to the aorta, the loss of the existing thrombosis to support and reinforce the graft, the unsuitability of the surgery for many patients having abdominal aortic aneurysms, and the problems associated with performing the surgery on an emergency basis after the aneurysm has ruptured. Further, the typical recovery period is from one to two weeks in the hospital and a convalescence period, at home, ranging from two to three months or more, if complications ensue. Since many patients having abdominal aortic aneurysms have other chronic illnesses, such as heart, lung, liver and/or kidney disease, coupled with the fact that many of these patients are older, they are less than ideal candidates for surgery.

The occurrence of aneurysms is not confined to the abdominal region. While abdominal aortic aneurysms are generally the most common, aneurysms in other regions of the aorta or one of its branches are possible. For example, aneurysms may occur in the thoracic aorta. As is the case with abdominal aortic aneurysms, the widely accepted approach to treating an aneurysm in the thoracic aorta is surgical repair, involving replacing the aneurismal segment with a prosthetic device. This surgery, as described above, is a major undertaking, with associated high risks and with significant mortality and morbidity.

Over the past five years, there has been a great deal of research directed at developing less invasive, endovascular, i.e., catheter directed, techniques for the treatment of aneurysms, specifically abdominal aortic aneurysms. This has been facilitated by the development of vascular stents, which can and have been used in conjunction with standard or thin-wall graft material in order to create a stent-graft or endo-graft. The potential advantages of less invasive treatments have included reduced surgical morbidity and mortality along with shorter hospital and intensive care unit stays.

Stent-grafts or endoprostheses are now Food and Drug Administration (FDA) approved and commercially available. Their delivery procedure typically involves advanced angiographic techniques performed through vascular accesses gained via surgical cut down of a remote artery, which may include the common femoral or brachial arteries. Over a guidewire, the appropriate size introducer will be placed. The catheter and guidewire are passed through the aneurysm. Through the introducer, the stent-graft will be advanced to the appropriate position. Typical deployment of the stent-graft device requires withdrawal of an outer sheath while maintaining the position of the stent-graft with an inner-stabilizing device. Most stent-grafts are self-expanding; however, in some cases an additional angioplasty procedure, e.g., balloon angioplasty, may be required to secure the position of the stent-graft. Most stent-grafts for percutaneous treatment of abdominal aortic aneurismal disease frequently have a proximal portion or trunk with a single proximal lumen that then bifurcates into two distal lumens of a smaller diameter than the diameter of said proximal portion. The distal lumens may have equal or unequal lengths. The proximal trunk portion of this bifurcated stent graft, being in fluid communication with each of the two distal lumens allows for uninterrupted fluid flow though the entire stent graft while excluding any flow into the aneurismal space.

Due to the large diameter of the above-described devices, typically greater than twenty French (F) (whereas 3 F=1 mm), arteriotomy closure typically requires suturing to facilitate the healing process. Some procedures may require additional surgical techniques, such as hypogastric artery embolization, vessel ligation, or surgical bypass in order to adequately treat the aneurysm or to maintain blood flow to both lower extremities. Likewise, some procedures will require additional advanced catheter directed techniques, such as angioplasty, stent placement and embolization, in order to successfully exclude the aneurysm and efficiently manage leaks.

As one increases the profile of the device, the difficulty in delivering the device also increases. The market today is populated by devices approximately 20 F and greater requiring the need for a surgical cut-down approach utilizing catheters, guidewires and accessory devices. Although devices of this size may substantially eliminate the need for open surgical intervention and the cut-down approach significantly reduces the acute complications that often accompany open surgical intervention, the ultimate goal and the market trend is to reduce delivery system profiles below 20 F, and thus be able to perform the procedure of delivering an endoprosthesis percutaneously, as by the Seldinger technique, which eliminates the need for the cut-down procedure.

Given the large profile of Abdominal Aortic Aneurysm devices, there is a significant motivation to reduce profile. In order to reduce profile, the stents comprising the bifurcated legs are sometimes staggered relative to one another so that they are nested during delivery. By staggering the stent components of the bifurcated section, although a reduced profile can be achieved, the column strength of each leg may be somewhat compromised, this may in turn lead to a cannulation difficulties into the bifurcated legs. An alternative method in which to accomplish a reduction in overall profile is to assemble the resulting stent graft in the vessel by delivering the portions or sections of the device individually. With individual delivery of the portions, the overall resulting profile may be significantly reduced for each individual portion relative to the overall resulting profile in the situation when the entire device is delivered simultaneously. With a staged delivery as described, cannulation of the previously implanted portion is critical in locating the subsequently delivered portion and to ensure that inter-operative assembly of the individual portions is successful.

In addressing Abdominal Aortic Aneurismal disease, frequently, the initial stent-graft will be supplemented by the use of one or more additional stent-grafts, also known as endo-legs. By delivering the endo-legs separately, one can achieve the previously stated objective of reduced profile. The purpose of these endo-legs allows extension of one or both of the distal lumens of the initial stent-graft into each of the corresponding iliac arteries to allow for a continuous and uninterrupted flow path from the aorta into the respective iliac arteries and to ensure complete exclusion of the aneurysm. To ensure the continuous flow path, proper placement and securing of the endo-leg into the corresponding distal lumen of the initial stent graft is critical. Improper placement of the endo-leg may result in poor fixation and/or anchoring of the device. In addition improper placement may result in a poor fit of the endo-leg in the distal lumen of the initial stent-graft, which may result in endo-leaks as the uninterrupted flow path would be compromised.

While the above-described endoprostheses represents a significant improvement over conventional surgical techniques, there is a need to improve the endoprostheses, particularly their method of use and delivery and their applicability to varied biological conditions. Accordingly, in order to provide a safe and effective means for treating aneurysms, including abdominal aortic aneurysms as well as other cases where bifurcated stents or stent-grafts are utilized, a number of difficulties associated with currently known endoprostheses and their delivery systems must be overcome. One concern with the use of endoprostheses as described above, specifically the efficient and proper placement of an extension leg, is the ease of which access to the lumen of the device, or in the case of an abdominal aortic aneurismal device, the ease of which access to the contralateral leg of the initial stent-graft with a guide-wire can be achieved. This ease of use is directly correlated to the time required to achieve this objective, with time in this case being the interventionalist's enemy.

With the placement of abdominal aortic aneurismal devices, the trunk and distal lumen portions of the device are usually delivered with a delivery system that frequently utilizes a first guidewire, commonly referred to as the ipsilateral guidewire. Typically, said trunk and one of the distal lumens of the device tracks over said ipsilateral guidewire, meaning the ipsilateral guidewire is positioned within the interior of the device, through the trunk and one of the distal lumens of the initial graft. Proper placement of the guidewire essentially facilitates proper placement of the trunk portion and one of the distal lumen portions as well as at least one of the endo-legs providing an extension of the distal lumen when the corresponding endo-leg is subsequently delivered over said ipsilateral guidewire.

With the first endo-leg properly positioned, access to the contra-lateral leg of the device is normally performed with a second guidewire, and achieved by feel and experience of the physician directing the guidewire external to the body to control movement within the vessel augmented by the real-time fluoroscopic image provided. This can be an extremely difficult and time consuming task in normal vessels and the difficulty and time may significantly increase in tortuous vessels, highly angulated vessels, partially diseased vessels, calcified vessels, odd shaped vessels, short vessels, and/or long vessels all of which are quite common. The addition of both time and difficulty to the procedure may affect patient outcome. It is also desirable to limit exposure time to the various contrast agents utilized that enable real-time fluoroscopic imaging.

Accordingly, there exists a need for obtaining quick, easy, and efficient access of guidewires into the lumen of a previously placed device. It would be particularly advantageous to facilitate placement of a guidewire into the contralateral leg of an abdominal aortic aneurismal device.

In placing abdominal aortic aneurismal devices, it would also be advantageous to utilize in some way the existing delivery system over the first guidewire that placed the initial graft, to facilitate placement of the second guidewire into the contra-lateral leg of the initial graft given the relationship of the locations of the first and second guide-wires ordinarily used in such a procedure.

SUMMARY OF THE INVENTION

The guiding device of the delivery system of the present invention allows one to overcome the difficulties associated with the methods and devices currently in use for obtaining contra-lateral leg access of the device to be implanted in order to treat both aneurysms and other related vascular diseases, as briefly described above, as well as being useful in other applications where access to a lumen requires facilitation.

In one embodiment of the invention, an intraluminal delivery device comprises an elongate inner tubular member having a proximal region and a distal region and being adapted to engage over a guidewire. The distal region of the elongate inner tubular member is configured to receive a bifurcated intraluminal device having a first tubular leg and a second tubular leg. The first and the second tubular legs each have a distal opening, wherein the distal region of the elongated inner tubular member is positioned within the first leg. The intraluminal delivery device further includes a pre-loaded guidewire segment having a length shorter than the elongated inner tubular member. The pre-loaded guide-wire segment is attached to the inner tubular member and positioned within the second leg and extending there through.

In another embodiment of the invention, a pre-loaded wire is loaded into the prosthesis and delivery catheter at the time of manufacture and positioned to be within or extend beyond the contra-lateral leg during implantation. This allows the user to capture this wire with use of a snare and obtain contra-lateral leg access with a second guidewire. At this point a catheter may be advanced over the snare and wire to allow for placement of a second prosthesis secured within the contra-lateral leg of the first prosthesis.

In accordance with another aspect, the present invention is directed to a method for treatment of aneurismal disease in an artery wall. More specifically the present invention is directed to a method to obtain contra-lateral leg access of a Bifurcated Stent or Bifurcated Stent Graft. Specifically the method in accordance with the present invention comprises the controlled delivery of an initial bifurcated stent graft for the treatment of abdominal aortic aneurismal disease or other vascular diseases. The guiding device of this delivery system in accordance with the present invention allows for and facilitates access to the contra-lateral lumen of the initial bifurcated stent graft by directing the second guidewire into the contra-lateral leg. The guiding device achieves this by providing a larger target or opening diameter to receive the second guidewire and is positioned to allow for direct entry of the guidewire into the contra-lateral lumen. Upon initial deployment of the contra-lateral endo-leg, the expandable member may be released having performed its function, because the guidewire passed through the interior of the expandable member, the same is true for the second endo-leg, which prevents any additional migration or movement of the expandable member given that once the endo-leg is fully deployed after release of the expandable member, the outward diametrical expansion of the endo-legs retains the position of the expandable member since the expandable member is concentrically wrapped around the endo-leg. At this point the endo-leg for the ipsilateral distal lumen can be delivered over the first guide wire. Alternately in accordance with the present invention, one may utilize the pre-loaded wire in the prosthesis, which upon capturing with a snare may allow for easier contra-lateral leg access.

In accordance with another aspect of the invention, the intraluminal device has a main body including a proximal trunk portion and distal first and second tubular leg portions, and a separate and detached endo-leg portion. The method of delivering the intraluminal device to the location in a body lumen includes delivering a first delivery device to a location in the body lumen. The first delivery device includes a first elongate member and a pre-loaded wire attached thereto, and carries the main body of the intraluminal device such that the first elongate member extends through the proximal trunk portion and distal first leg portion of the intraluminal main body portion. The main body of the intraluminal device is deployed at the location in the body lumen, and the first delivery device is positioned within the main body of the deployed intraluminal device such that a free end of the pre-loaded wire extends into the second leg of the intraluminal main body portion. A second delivery device having a second elongate member is delivered to the location in the body lumen. The second elongate member includes a capturing mechanism associated therewith, configured for grasping the pre-loaded wire. The second delivery device also carries the endo-leg of the intraluminal device. The process further includes grasping the pre-loaded wire with the capturing mechanism associated with the second delivery device, advancing the second elongate member into the lumen of the second tubular leg to position the endo-leg in the desired location and deploying the endo-leg.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

The present invention is directed to an endovascular delivery system for use in treating or repairing aneurysms. Systems for treating or repairing aneurysms come in many forms. The systems for treating Abdominal Aortic Aneurysms typically include an anchoring and/or sealing component which is positioned in healthy tissue above the aneurysm and one or more grafts which are in fluid communication with the anchoring and/or sealing component and extend through the aneurysm and anchor in healthy tissue below the aneurysm. This results in an uninterrupted flow path from one portion of the artery to another thereby bypassing the diseased portion of the artery by isolating the flow path through the diseased portion of the artery.

Current systems are preferably percutaneously delivered and deployed. The conventional delivery system comprises an elongated inner tube or member having both a proximal and distal region wherein the distal region of the inner tube is configured to receive and intraluminal device such as a stent, stent graft or other intraluminal device. The delivery device also comprises a sheath, which is positioned concentrically around at least a portion of the inner member and at least partially covers the intraluminal device positioned on the inner member. This construct is assembled such that when movement of the inner member relative to the sheath occurs, the intraluminal device moves with the inner member and becomes uncovered by the sheath allowing for the intraluminal device to be deployed either by self-expanding means when the stent is fabricated from a shape memory alloy or be expanded by the application of an outwardly directed radial force on the inner surface of the stent accomplished with a inflatable balloon mounted on the inner member and positioned beneath the intraluminal device.

The cannulation guiding device and method of use of the present invention may be utilized to effectively reduce operative time required to prevent and treat abdominal aortic aneurismal disease by facilitating placement of the contra-lateral guidewire within the intraluminal medical device. Although the treatment of this disease continues to advance, as stated above the operator may encounter difficulties in gaining access to the contra-lateral leg of the deployed device, especially in the more tortuous vessels, thereby potentially extending the surgical time required to complete the procedure. Although the present invention may be utilized in other procedures and diseases where similar difficulties are encountered or similar access is required, the exemplary embodiments of the present invention will be described with respect to the treatment of Abdominal Aortic Aneurismal Disease. In addition, a methodology will be described for the effective delivery of abdominal aortic aneurismal devices using a cannulation guiding device in accordance with the present invention.

Figure 1:
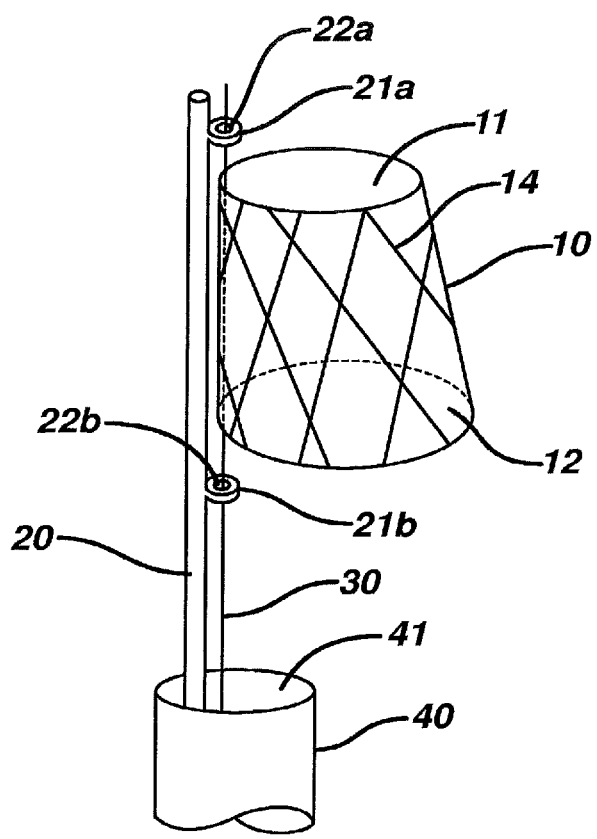
FIG. 1 is a perspective view of a first embodiment of a cannulation guiding device in the deployed state in accordance with the present invention.

Referring to FIG. 1, the illustration depicts a first embodiment of a cannulation guiding device in accordance with the present invention. For ease of explanation and clarity, only the distal region of the device is illustrated in this and the following figures, as the remaining proximal portion of the device is substantially similar to conventional delivery devices. In this embodiment the system is comprised of an expandable member (10) having a proximal opening (12) and distal opening (11) and an intermediate conduit between said proximal and distal openings. The expandable member may be releasably attached to an inner member (20) of a delivery system by means of a release wire (30). This may be accomplished by incorporating features such as release wire guides (21*a* & 21*b*) axially positioned on the inner member (20) adapted to receive the release wire (30) by having the release wire (30) pass through the openings (22*a* & 22*b*) of the release wire guides (21*a* & 21*b*). This entire construct is shown in the deployed state, having been advanced distally relative to the delivery sheath (40) and upon exiting the opening (41) of the delivery sheath (40) is no longer constrained by said delivery sheath (40). Alternatively, the delivery sheath (40) may be moved proximally to expose the construct. The expandable member (10) although not a requirement may preferably be conically shaped in that the diameter of the proximal opening (11) is smaller than the diameter of the distal opening (12). The expandable member (10) may also be augmented with a stent structure (14), which may serve to define the deployed shape of the member. Stent structure (14) may be fabricated from shape memory alloys or more traditional metallic alloys. In each case an inflatable member may be used to expand the device or alternately augment expansion. Alternately, expandable member (10) may be fabricated from nitinol thin film that may allow expansion without the need for stent structure (14).

Figure 2:
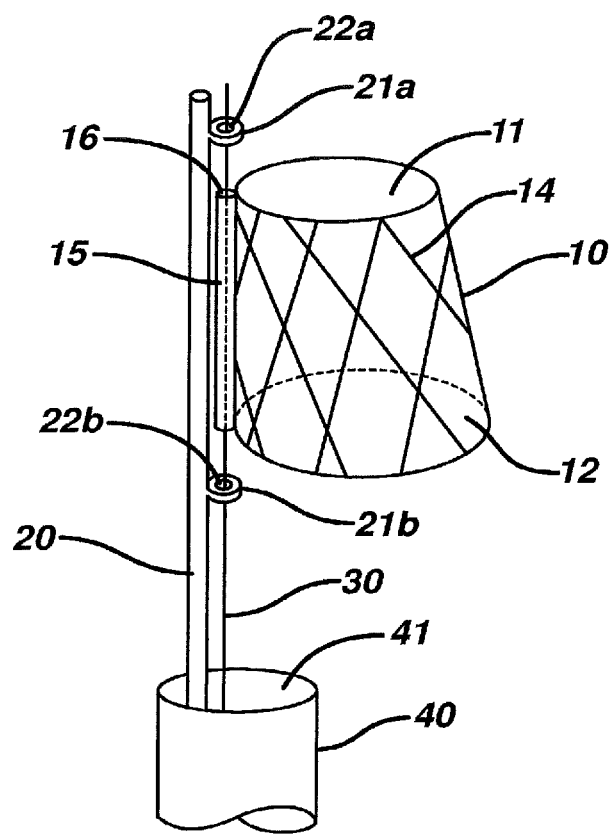
FIG. 2 is a perspective view of a second embodiment of a cannulation guiding device in the deployed state in accordance with the present invention.

In an alternative embodiment, expandable member (10) incorporates a guiding tube (15), which defines a lumen (16) adapted to freely slide and rotate relative to and about release wire (30) as shown in FIG. 2. Extent of axial movement of expandable member (10) can be controlled by relative axial positioning of release wire guides (21*a* & 21*b*). Increasing the axial distance between release wire guides (21*a* & 21*b*) on inner member (20) results in increased extent of travel of expandable member (10). Decreasing the axial distance between release wire guides (21*a* & 21*b*) on inner member (20) results in decrease extent of travel of expandable member (10). In this embodiment it is preferred that the lumen (16) of guiding tube (15) is appropriately sized to release wire (30) to allow for suitable controlled movement of expandable member (10). In this embodiment and the previous embodiment, axial retraction of the release wire (30) relative to the inner member (20) allows for the release of the expandable member (10) from the inner member (20). Once released, the inner member (20) and release wire (30) can be retracted within the sheath (40) allowing for the entire delivery system to be safely removed from the vasculature leaving behind the expandable member (10).

Figure 3:
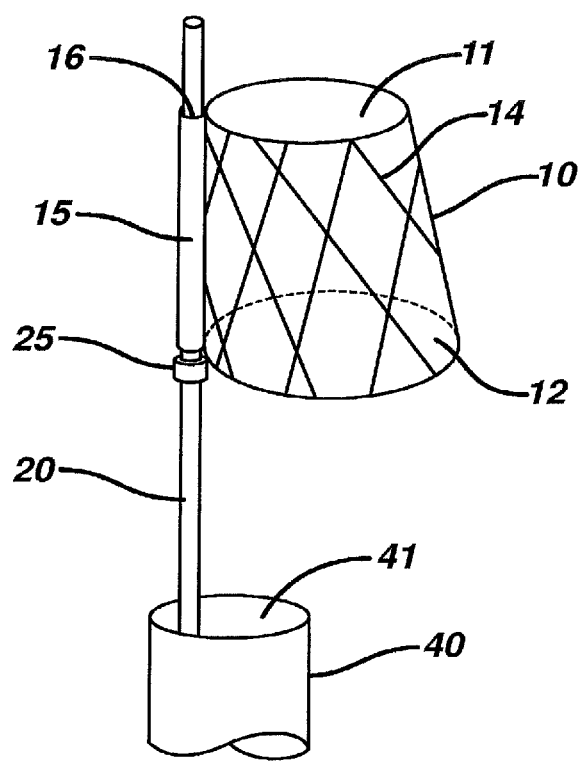
FIG. 3 is a perspective view of a third embodiment of a cannulation guiding device in the deployed state in accordance with the present invention.

As shown in FIG. 3, in yet another alternate exemplary embodiment, the release wire (30) is optional in accordance with the present invention. In this embodiment the expandable member (10) once again incorporates a guiding tube

(15) having a longitudinal lumen (16) adapted to slide over inner member (20) which is preferably configured with an axial stop (25) to prevent additional axial movement of expandable member (10) beyond that of axial stop (25) located on inner member (20). Axial stop (25) allows for any forward movement of inner member (20) to be transmitted to expandable member (10). In this embodiment, expandable member (10) is free to rotate relative to and about inner member (20). Expandable member (10) may also be operatively attached to inner member to prevent rotation with use of a keyed slot. (not shown) Limiting rotational movement of expandable member, and temporarily stitching the two distal lumens of the first portion of the intraluminal device together may improve alignment of the cannulation device with the contralateral distal lumen in the more difficult cases as well as in cases where the extension lengths of each of the distal lumens of the intraluminal device are not equivalent. Any required offsets of the cannulation device equivalent to the spacing of the distal lumens of the delivered intraluminal device may be achieved by modifying the spacing of the cannulation guiding device from that of the inner member to accommodate different configurations of intraluminal devices.

Figure 4:
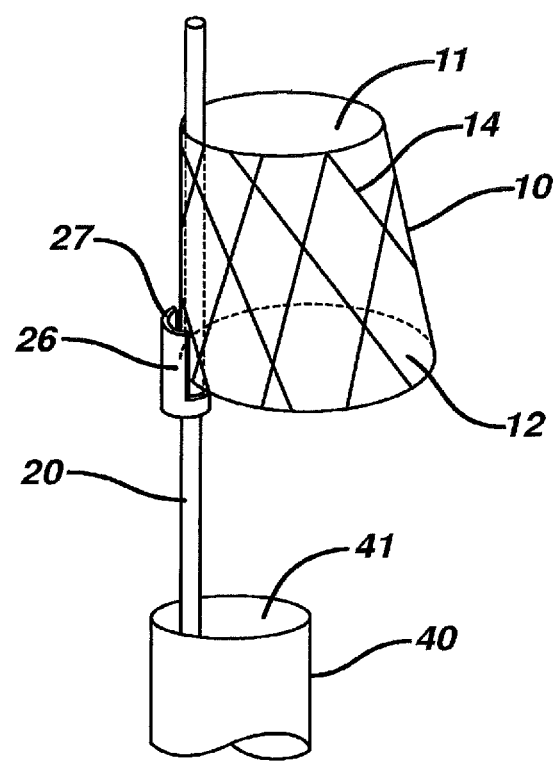
FIG. 4 is a perspective view of a fourth embodiment of a cannulation guiding device in the deployed state in accordance with the present invention.

As shown in FIG. 4, in yet another alternate exemplary embodiment, the release wire (30) is optional and the need for the guiding tube (15) is no longer required. In this embodiment in accordance with the present invention modified axial stop (26) includes an extended shoulder (27) to limit radial translation of expandable member (10) relative to inner member (20). As in the previous embodiment, the axial stop (26) allows for any forward movement of inner member (20) to be transmitted to expandable member (10), while limiting the additional axial movement of expandable member (10) beyond that of axial stop (26) in the direction towards delivery sheath (40). In this embodiment, relative rotation of the expandable member (10) relative to the inner member (20) is allowed, as is limited translation in the radial plane and relative movement in the axial direction as described above. But both rotation and translation may also be constrained with the use of stops and keyways if desired.

Figure 5:
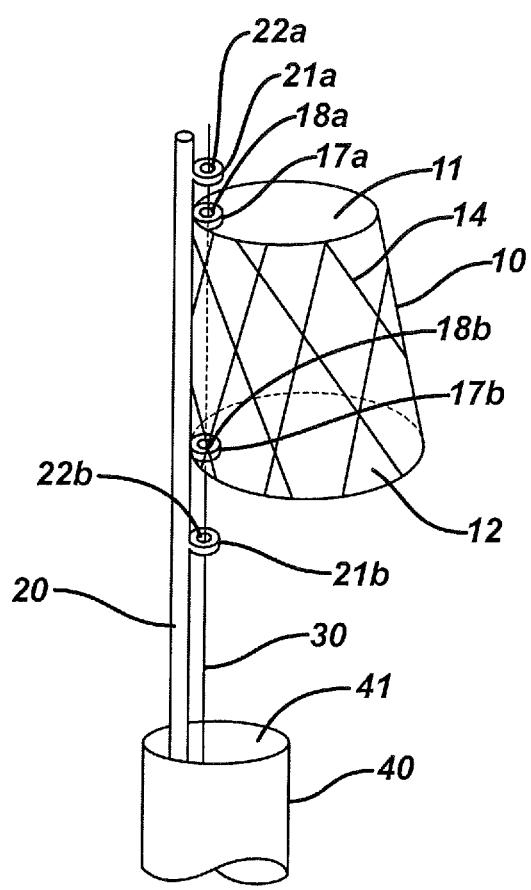
FIG. 5 is a perspective view of a fifth embodiment of a cannulation guiding device in the deployed state in accordance with the present invention.

As shown in FIG. 5, alternate configurations and locations of the guiding tube (15) are possible. In this embodiment, the guiding tube (15) is replaced with two guide rings (17a & 17b) each having an opening (18a & 18b) adapted to receive the release wire (30). In this embodiment the expandable member (10) is free to rotate about the release wire (30) while limited axial movement is controlled by the presence and placement of the release wire guides (21a & 21b).

Figure 7A:
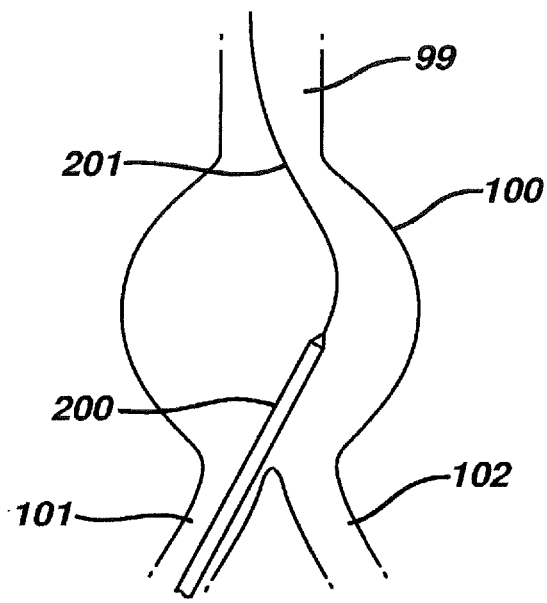
FIGS. 7*a* through 7*h* provide a diagrammatic representation of the process of how a cannulation guiding device would be utilized to facilitate gaining access to the contra-lateral leg of an abdominal aortic aneurismal device in accordance with the present invention.
Figure 7B:
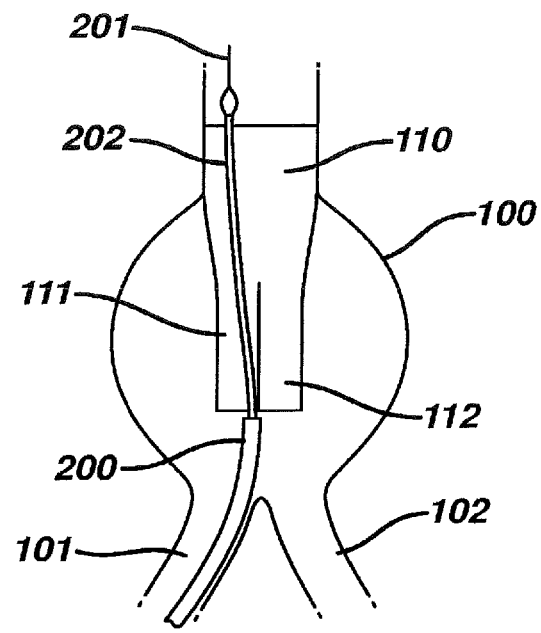
Figure 7C:
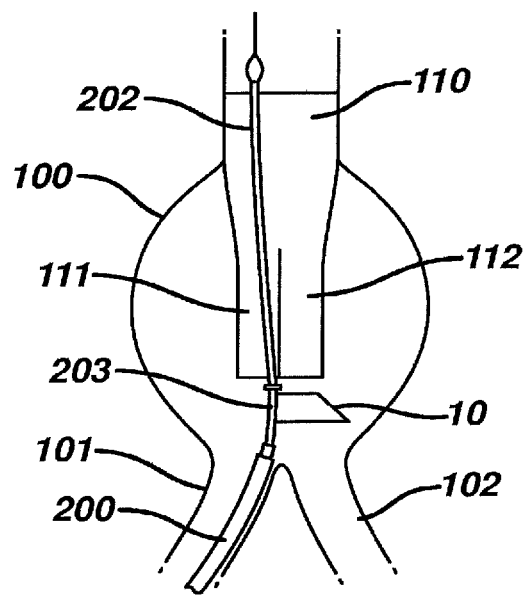
Figure 7D:
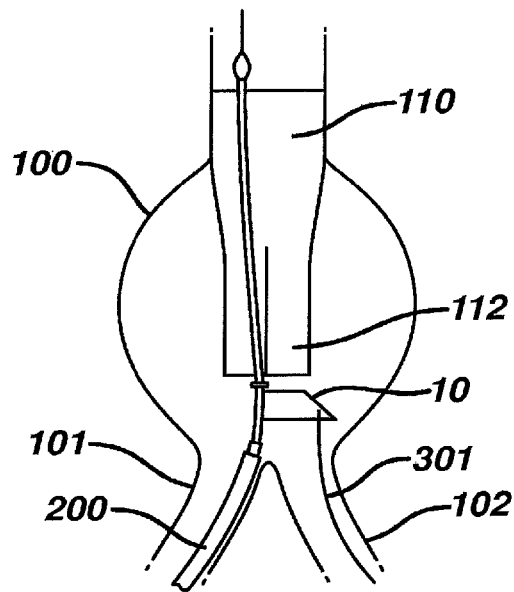
Figure 7E:
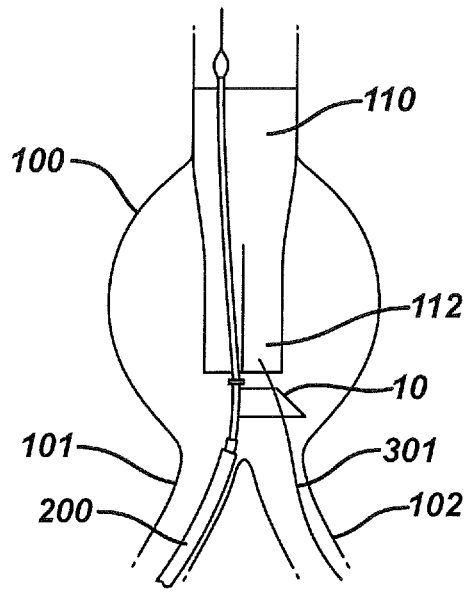
Figure 7F:
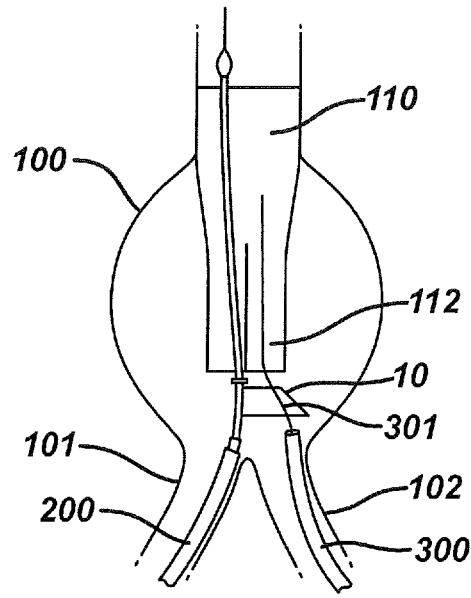
Figure 7G:
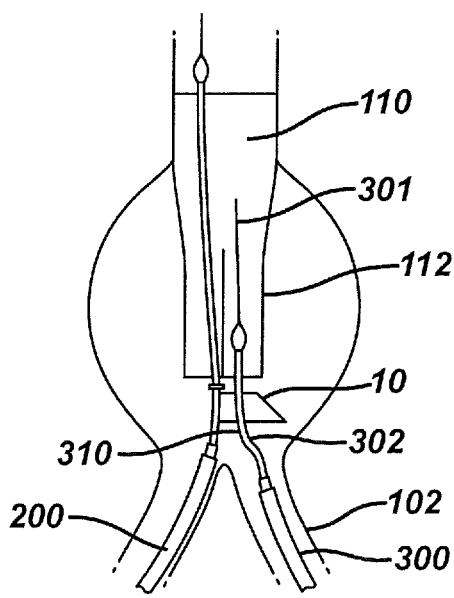
Figure 7H:
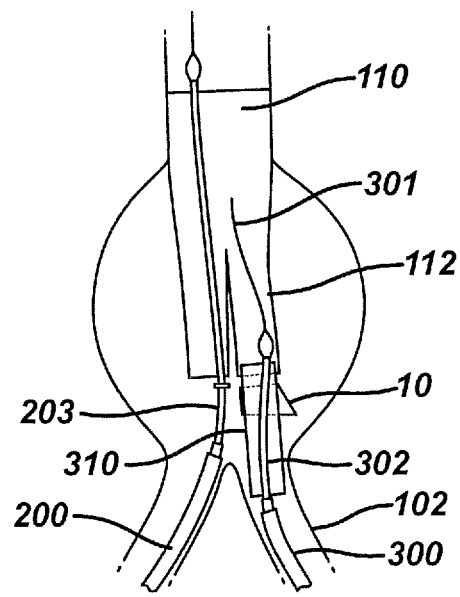

In accordance with the present invention, delivery of the intraluminal device is greatly enhanced by significantly reducing operative time by facilitating access to the contra-lateral leg of a bifurcated intraluminal medical device. As shown in FIG. 7a, a first delivery system (200) is delivered over a first guidewire (201) through one of the iliac arteries (101) into the aneurismal sac (100) and up into the descending aorta (99). With the delivery system (200) properly positioned with the aid of fluoroscopy, the first portion of the intraluminal device (110) is deployed from the inner member (202) of the delivery system (200) securing the trunk portion into the healthy portion of the descending aorta (99) leaving the two distal lumens (111 & 112) positioned within the aneurismal sac space (100) as shown in FIG. 7b. Advancing the inner member (202) of the first delivery system (200) further, deploys the cannulation guiding member (10) from inner member (203) in accordance with the present invention as shown in FIG. 7c. The location and shape of the cannulation guiding device (10) is positioned such that upon delivery of a second guidewire (301), delivered up the other iliac artery (102), allows for the tip of guidewire (301) to enter the interior of the cannulation guiding member (10) as shown in FIG. 7d, and upon additional forward movement, the guidewire (301) is directed into the distal lumen (112) of the intraluminal device (110) facilitated by the cannulation guiding member (10) as shown in FIG. 7e. This is followed by delivery of a second delivery system (300) over the second guide wire (301) up through the other iliac (102) as shown in FIG. 7f. With the second delivery system (300) positioned such that the inner member (302) of the second delivery system (300) passes through the expandable member (10) of the cannulation guiding device and into the distal lumen (112) of the intraluminal device (110), one is ready to deploy a second intraluminal device (310) as shown in FIG. 7g. The second intraluminal device (310) in this situation is an endo-leg that upon deployment is anchored into the distal lumen (112) of the intraluminal device (110) and the opposing end of the second intraluminal device (310) is anchored in the iliac (102) as shown in FIG. 7h. In addition, the expansion of the endo-leg (310) being positioned within the interior of the expandable member (10) fixes the expandable member (10) to the exterior of the endo-leg (310) after release from the inner member (203) of the first delivery system (200). The procedure is completed with deployment of a second endo-leg (not shown) from the first delivery system (200) allowing an uninterrupted flow path from the descending aorta into both of the iliac arteries (101 & 102).

In accordance with an alternative embodiment of the present invention, facilitating access to the contra-lateral leg of a bifurcated intraluminal medical device can also be achieved by augmenting or replacing the cannulation guiding member (10) with a suture loop (113). FIGS. 8a through 8h provide a diagrammatic representation of the steps showing how the use of one or more suture loops can, in this case, replace the cannulation guiding member and still achieve the desired effect. While the cannulation guiding member is not shown in FIGS. 8a through 8h, it should be noted that the present invention is not restricted to simply one or the other to facilitate contralateral access, but rather that each component (i.e. one or more suture loops as shown in FIGS. 8a through 8h, or the cannulation guiding member as shown in FIGS. 7a through 7h) used alone or in combination may be utilized to achieve the desired effect.

Figure 8A:
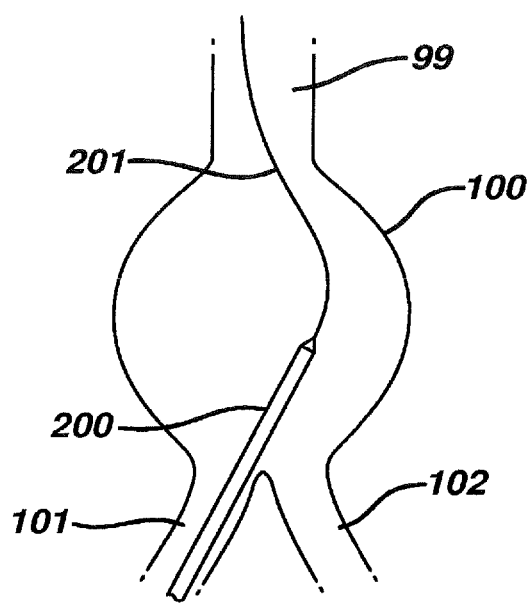
FIGS. 8*a* through 8*h* provide a diagrammatic representation of the process of how a cannulation guiding device would be utilized to facilitate gaining access to the contra-lateral leg of an abdominal aortic aneurismal device having a suture loop in place to maintain the position of the contralateral leg in accordance with the present invention.
Figure 8B:
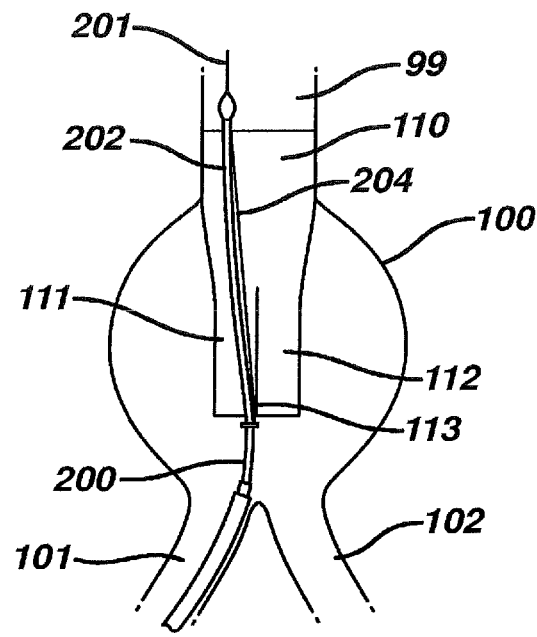
Figure 8C:
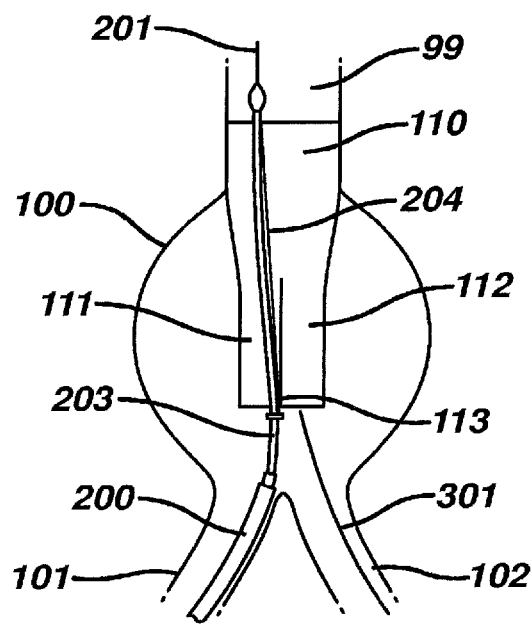
Figure 8D:
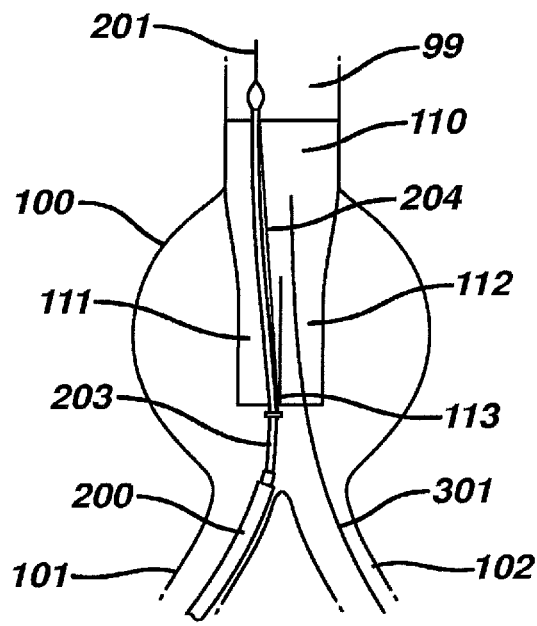
Figure 8E:
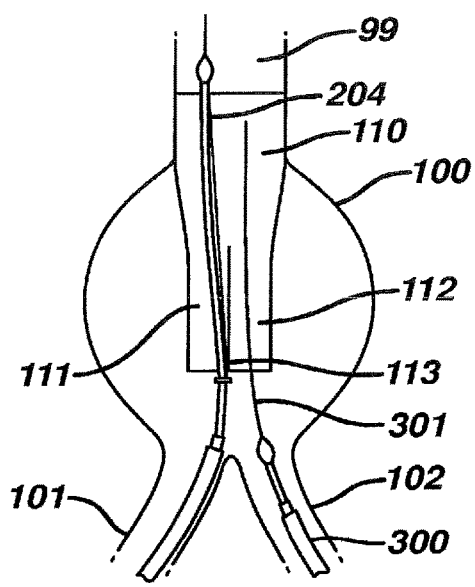
Figure 8F:
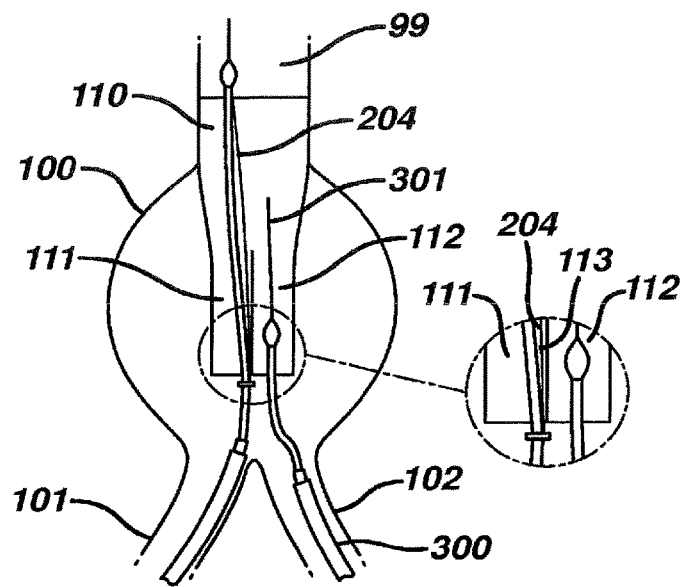
Figure 8G:
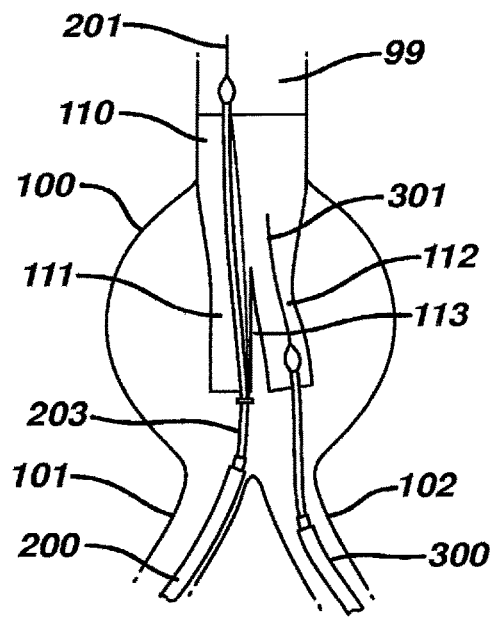
Figure 8H:
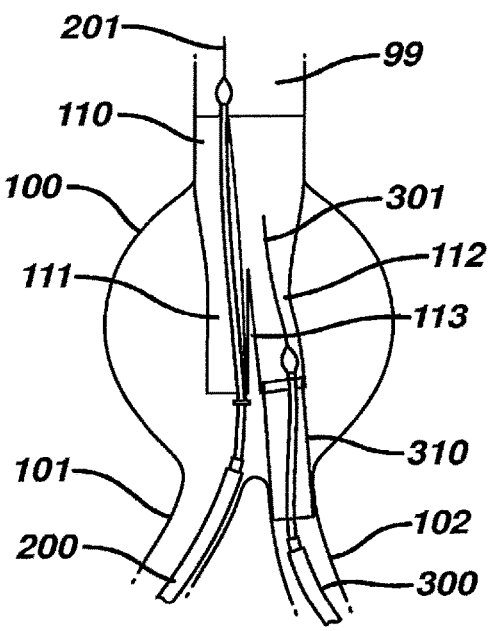

As shown in FIG. 8a, a first delivery system (200) is delivered over a first guidewire (201) through one of the iliac arteries (101) into the aneurismal sac (100) and up into the descending aorta (99). With the delivery system (200) properly positioned with the aid of fluoroscopy, the first portion of the intraluminal device (110) is deployed from the inner member (202) of the delivery system (200) securing the trunk portion into the healthy portion of the descending aorta (99) leaving the two distal lumens (111 & 112) positioned within the aneurismal sac space (100) as shown in FIG. 8b. Release wire (204) is positioned both alongside inner member 202 and within distal lumen (111) and passes through suture loop (113). Suture loop (113) is attached to distal lumen (112) passing through the wall of distal lumen (111). The release wire (204) which passes through suture loop (113) serves to lock the two distal lumens (111 & 112) adjacent to each other and also provides additional column strength to the distal lumen (112). Although not shown, additional suture loops positioned above and/or below suture loop (113) may be utilized to increase the degree of locking of the two distal lumens further. The presence of additional suture loops would also serve to increase the column strength further. Because of this additional column strength provided, and somewhat fixed location of the distal lumen (112), entry of a guidewire into the distal lumen (112) is simplified, more reliable and consistent. As shown in FIGS. 8c and 8d, advancing a second guidewire (301), delivered up the other iliac artery (102), allows for the tip of guidewire (301) to enter the interior of the distal lumen (112) and upon additional forward movement, the guidewire (301) is directed into the distal lumen (112) of the intraluminal device (110) facilitated by the suture loop (113) locked onto the release wire (204) which serves not only to fix the position of distal lumen (112) adjacent to distal lumen (111), but also prevents the collapse of the opening of the distal lumen (112) due to the increased column strength. With the contralateral guidewire (301) positioned within distal lumen (112), delivery of a second delivery system (300) over the second guide wire (301) up through the other iliac (102) can be accomplished as shown in FIG. 8e. Further advancement of the second delivery system (300) occurs until the second delivery system is positioned within the distal lumen (112) as shown in FIG. 8f. The enlarged detail of FIG. 8f shows the distal end of the delivery system (300) positioned within the distal lumen (112) and shows the release wire (204) passing through suture loop (113) both being positioned within the adjacent distal lumen (111). As shown in FIG. 8g, before deploying a second intraluminal device (310) one withdraws the release wire (204) by pulling back release wire (204) relative to inner member (202) so that the release wire (204) is no longer constrained by the suture loop (113) and as such, distal lumen (112) is freed from being locked to and adjacent to distal lumen (111). With distal lumen (112) freed from distal lumen (111), manipulation of distal lumen (112) can occur if desired, by movement of the second delivery system (300) which is still located within the distal lumen (112). The second intraluminal device (310) in this situation is an endo-leg that upon deployment is anchored into the distal lumen (112) of the intraluminal device (110) and the opposing end of the second intraluminal device (310) is anchored in the iliac (102) as shown in FIG. 8h. The procedure is completed with deployment of a second endo-leg (not shown) from the first delivery system (200). The distal end of the second endo-leg would be fixed to the distal lumen (111) while the proximal leg would be anchored to the ipsilateral iliac (101) creating an uninterrupted flow path from the descending aorta into both of the iliac arteries (101 & 102).

Figure 6:
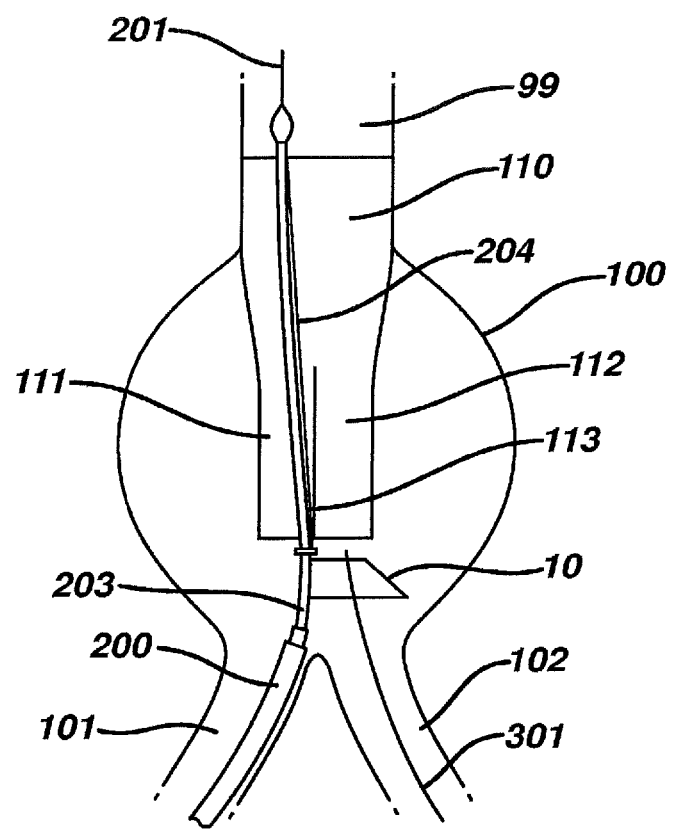
FIG. 6 is a perspective view of another embodiment of a cannulation guiding device in the deployed state in accordance with the present invention.

In a further embodiment, the expandable member (10) disclosed in FIGS. 1-7h can be combined with the suture loop (113), disclosed in FIGS. (8a) through (8h). This configuration, illustrated in FIG. 6, provides control over the location of the contra endo-leg (310), the ability to manipulate the contra endo-leg (310), and the ability to manipulate and guide the guidewire (301) from the second delivery system (300) into the contra luminal opening of the intraluminal device (110).

Figure 9:
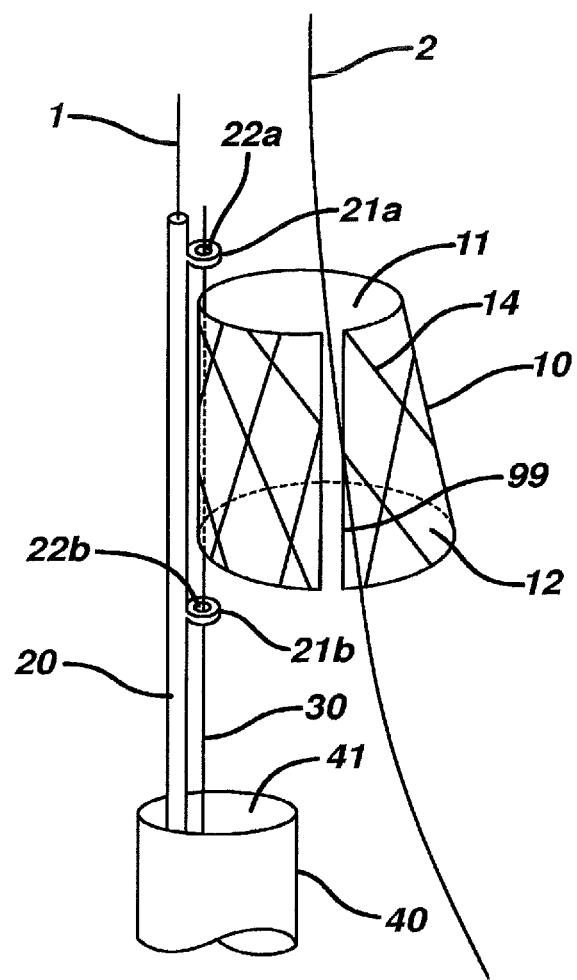
FIG. 9 is a perspective view of a modified embodiment of a deployed cannulation guiding device in accordance with the present invention.

As set forth above, in addition to releasing the expandable member (10) by retraction of the release wire (30), additional modifications to the embodiments include the expandable member (10) being fabricated with a longitudinal slit (199), as shown in FIG. 9, which may allow the expandable member to be easily removed from the release wire (30) without retracting the release wire (30), or alternately allowing the expandable member to be removed from the inner member (20) in those embodiments lacking a release wire (30) without any relative axial movement between the inner member (20) and expandable member (10). In an alternate embodiment the longitudinal slit (99) in the expandable member (10) may allow for guidance of the second guidewire (2) into the contra-lateral leg, and once achieved, allow for the expandable member (10) to be removed from the second guidewire (2) that was previously positioned within the interior of the expandable member (10).

In another alternate exemplary embodiment, the sheath of the delivery system may comprise an inner layer or coating on its inner surface which substantially prevents the expandable member (10) from becoming embedded therein while increasing the lubricity thereof. This inner layer or coating may be utilized with the sheaths illustrated in FIGS. 1 through 5, & 9 or as an alternative means to decrease the guiding device deployment forces. Given the thinness of the coating, the overall profile of the delivery system will be minimally impacted if at all. Any number of suitable biocompatible materials may be utilized for such a coating. In an exemplary embodiment, silicone based coatings may be utilized. Essentially, a solution of the silicone-based coating may be injected through the apparatus and allowed to cure at room temperature. The amount of silicone-based coating applied to the internal surface of the sheath (40) should be minimized to prevent transference of the coating to the expandable member or any additional intraluminal devices contained therein. In addition to increasing the strength of the sheath and making it more lubricious, the coating is extremely biocompatible which is important since it does make contact with blood, albeit at least temporarily.

Figure 10:
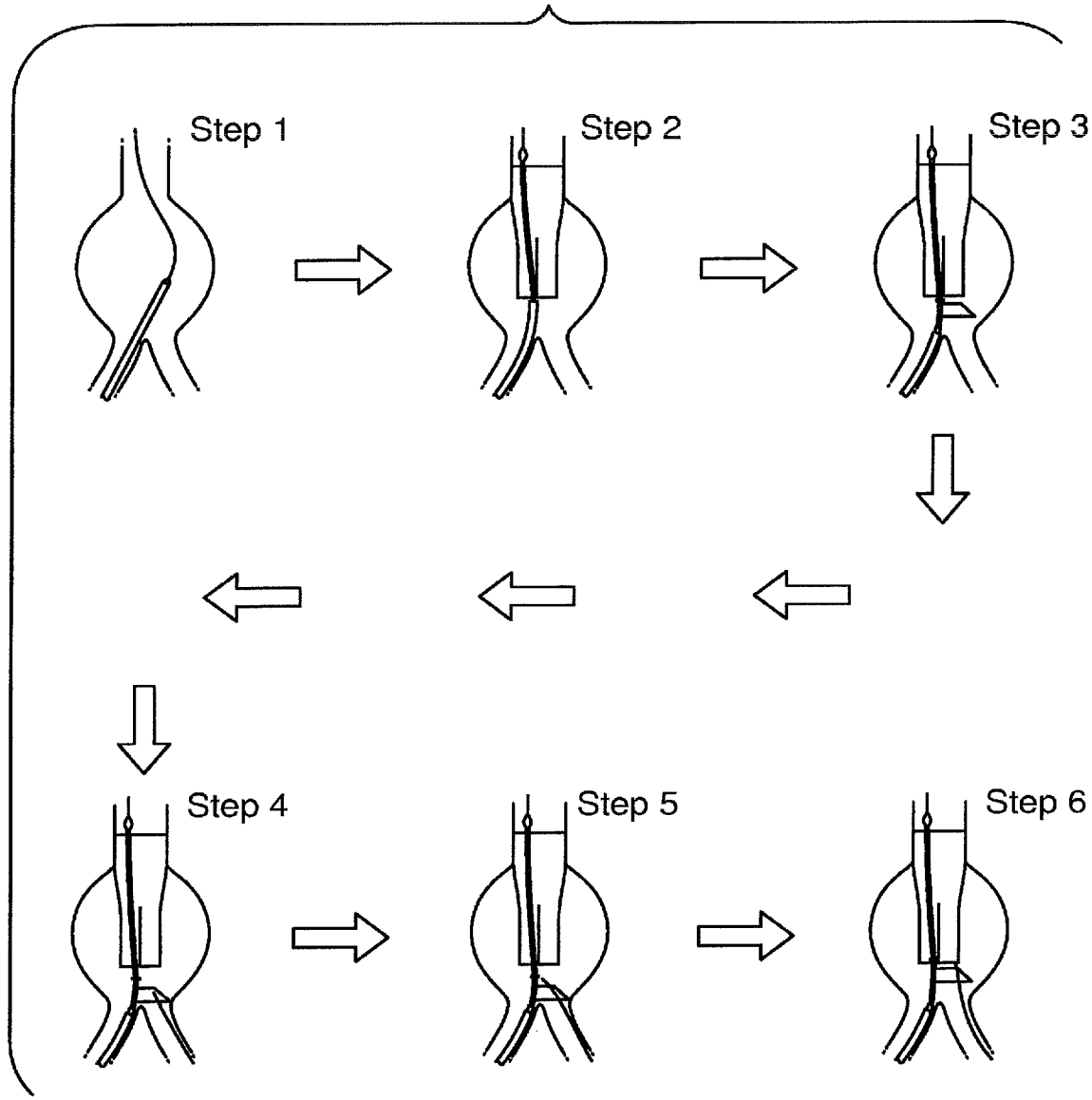
FIG. 10 shows the steps one may follow to facilitate placement of the contra-lateral guidewire within the cannulation guiding device by moving the cannulation guiding device down over guidewire in accordance with the present invention.

Placement of the guidewire within the cannulation guiding device may also be achieved by sliding the cannulation guiding device over the wire as shown in the steps indicated in FIG. 10. The first step shows the device delivery system being tracked over the ipsilateral guidewire. In step 2, the first portion of the intraluminal device is deployed and released from the delivery system. In step 3, the sheath of the delivery system is further retracted exposing the cannulation guiding device that extends eccentrically from the inner member to which it stays attached. The cannulation guiding device may then be positioned just above the aortic bifurcation and over the contra-lateral iliac artery by a combination of torque and axial translations allowing the contra-lateral guidewire to be tracked and guided into the cannulation guiding device as shown in step 4 in accordance with the present invention. Once the contra-lateral guidewire is captured within the cannulation guiding device, the contra-lateral guidewire is tracked through the cannulation guiding device as shown in step 5. Both the contra-lateral guidewire and the cannulation guiding device can then be advanced together to gain access with the contra-lateral guidewire into the contra-lateral leg of the delivered intraluminal device as shown in step 6 of FIG. 10. The contra-lateral delivery system may then be tracked over the contra-lateral guidewire through the cannulation guiding device. In each of these steps, visualization of the process may be enhanced with fluoroscopy.

Figure 11A:
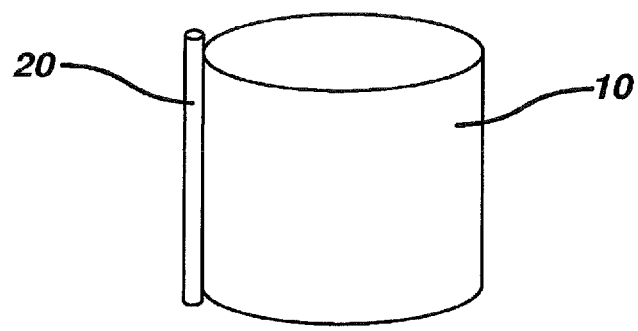
FIGS. 11*a* & 11*b* show a modified embodiment of the expandable member of the present invention operatively attached to the inner member both in the deployed state as well as the deployed and subsequently unconstrained state.
Figure 11B:
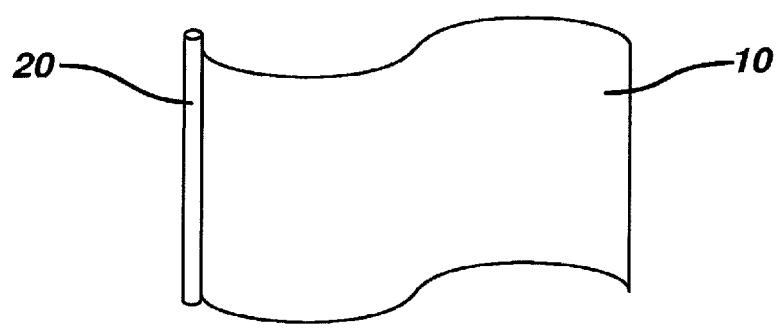

The expandable member (10) may also be fabricated from shape memory alloy, which may allow a pre-defined shape to be programmed. Particularly in accordance with the present invention, the expandable member may be formed from a sheet with one end fixed to inner member (20) and the other end operatively attached to inner member (20) such that when both ends are attached to inner member (20) the guiding conduit of the expandable member (10) is formed as shown in FIG. 11a. This is in contrast to when the operatively attached end is unconstrained and the sheet is allowed to return to its pre-programmed shape as shown in FIG. 11b. This unfurling of the guiding conduit allows the first delivery system to become decoupled from the second delivery system and/or second guidewire which facilitates movement and/or removal of the first delivery system independent of the second delivery system and/or second guidewire.

Figure 12:
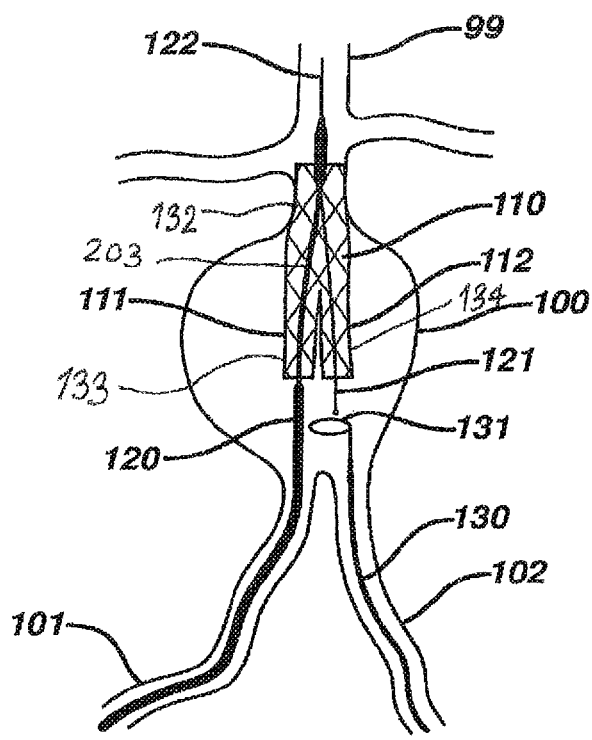
FIG. 12 is a diagrammatic representation of a first deployment system with the abdominal aortic aneurismal device deployed having a pre-loaded wire positioned within the contra-lateral leg which facilitates access to said leg in accordance with the present invention.

In an alternate embodiment of the present invention, a pre-loaded wire (121) can be incorporated into the delivery device (120) and bifurcated intraluminal device (110) as shown in FIG. 12. In the illustrated embodiment, the bifurcated intraluminal device (110) includes a tubular trunk section (132) and distal lumens (111) formed by first and second tubular legs (133, 134), respectively. The pre-loaded guidewire segment (121) has a length shorter than the elongated inner tubular member (203), and is attached to the inner tubular member (203) and positioned within the second leg (134) of the bifurcated intraluminal device (110). The free end of the pre-loaded guidewire (121) extends through the second leg (134) of the bifurcated intraluminal device (110), and preferably extends past the distal opening of the second leg (134).

The pre-loaded guidewire segment (121) may be attached to the inner tubular member (203) of the delivery device (120) at a point proximal the bifurcation point between the trunk section (132) and the first and second tubular legs (133, 134), within the trunk section (132) or distal to the bifurcated intraluminal device (110). The pre-loaded guidewire segment (121) may also have a feature on its free distal end to facilitate capture by the capture mechanism. The feature may include a geometric shape, such as a ball or bulbous end.

The intraluminal delivery device (120) may further include a sheath having a proximal end and a distal end positioned concentrically around at least a portion of the elongated inner tubular member (203) and the intraluminal device (110), wherein the sheath constrains the expansion of the intraluminal device (110) and whereby relative movement between the sheath and the inner tubular member (203) allows for the delivery of the intraluminal device (110). The sheath may further comprise a lubricous coating to assist relative movement between the sheath and the inner tubular member (203) and intra luminal device (110).

In this embodiment, the delivery device (120), which delivers the intraluminal device (110), is advanced through one of the iliac arteries (101) over a first guidewire (122), commonly referred to as the ipsilateral guidewire (122) to the location in the body lumen. The intraluminal device may be deployed from its radially constrained position by retraction of the sheath. The delivery device (120), after deploying the intraluminal device (110), remains positioned within the interior of the intraluminal device (110) in the region of both the trunk and one of the distal lumens (111). The pre-loaded wire (121), affixed to the delivery system (120), is positioned within the interior of the remaining (second) distal lumen (112) of the intraluminal device (110). In a preferred embodiment, the pre-loaded wire (121) extends beyond the opening of the distal lumen (112). With the intraluminal device (110) deployed, and the pre-loaded wire (121) extending beyond the distal lumen (112), access to the distal lumen (112) is easily accomplished with a capture mechanism, such as a snare (131) associated with the end of a second delivery system (130). The capture mechanism, which is typically delivered through the other iliac artery (102), is capable of grasping the pre-loaded wire (121). Once the capture mechanism (131) captures the pre-loaded wire (121), additional upward movement of the first delivery system (120) up the descending aorta (99) will bring the second delivery system (130) into the confines of the interior of the distal lumen (112) of the intraluminal device (110) and position the delivery system (130) for the subsequent deployment of the contra-lateral endo-leg.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A delivery device for use in an iliac artery comprising:
  a bifurcated intraluminal device having a first distal lumen and a second distal lumen adjacent to one another;
  a release wire positioned both alongside a first inner member and within the first distal lumen and passing through a suture loop wherein the suture loop is attached to the second distal lumen passing through the wall of the first distal lumen, wherein the release wire, which passes through the suture loop, serves to releasably constrain the first and second distal lumens adjacent to each other, wherein distal movement of the release wire relative to the bifurcated intraluminal device releases the constraint of the release wire, such that the second distal lumen is freed from being locked to and adjacent to the first distal lumen.

2. The delivery device of claim 1, wherein the first inner member is deliverable over a first guidewire.

3. The delivery device of claim 1, wherein additional suture loops are positioned along the wall of the first distal lumen to increase the degree of constraint of the first and second distal lumens.

4. The delivery device of claim 1, wherein the delivery device further comprises an endo-leg is anchored to the first distal lumen.

5. The delivery device of claim 1, wherein a first portion of the bifurcated intraluminal device is deployable from the first inner member.

6. The delivery device of claim 5, wherein the delivery device further comprises a cannulation guiding member shaped for allowing a tip of a guidewire to enter the interior of the cannulation guiding member.

7. The delivery device of claim 6, wherein the delivery device further comprises a second inner member, wherein the cannulation guiding member is deployable from the second inner member.

8. The delivery device of claim 7, wherein the cannulation guiding member is deployed by proximal advancement of the first inner member.

9. A delivery system comprising a first delivery device and a second delivery device for use in an iliac artery comprising:
  a first delivery device comprising:
    a bifurcated intraluminal device having a first distal lumen and a second distal lumen adjacent to one another; and
    a release wire positioned both alongside a first inner member and within the first distal lumen and passing through a suture loop wherein the suture loop is attached to the second distal lumen passing through the wall of the first distal lumen, wherein the release wire, which passes through the suture loop, serves to releasably constrain the first and second distal lumens adjacent to each other, wherein distal movement of the release wire relative to the bifurcated intraluminal device releases the constraint of the release wire, such that the second distal lumen is freed from being locked to and adjacent to the first distal lumen; and
a second delivery device comprising:
a second intraluminal device deployable from the second delivery device, wherein the second delivery device is positionable within the second distal lumen.

10. The delivery system of claim 9, wherein, once deployed, the second intraluminal device is anchored to the second distal lumen.

11. The delivery system of claim 9, wherein the second delivery device is deliverable over a second guidewire positionable within the second distal lumen.

* * * * *